United States Patent
Jenks

(10) Patent No.: US 10,429,014 B2
(45) Date of Patent: Oct. 1, 2019

(54) LIGHTING SYSTEM WITH GLARE REDUCING LIGHT ARRAY

(71) Applicant: William Chester Jenks, Rancho Cucamonga, CA (US)

(72) Inventor: William Chester Jenks, Rancho Cucamonga, CA (US)

( * ) Notice: Subject to any disclaimer, the term of this patent is extended or adjusted under 35 U.S.C. 154(b) by 0 days.

(21) Appl. No.: 15/875,354

(22) Filed: Jan. 19, 2018

(65) Prior Publication Data
US 2018/0202618 A1     Jul. 19, 2018

Related U.S. Application Data

(60) Provisional application No. 62/448,322, filed on Jan. 19, 2017.

(51) Int. Cl.
| | |
|---|---|
| *F21L 14/02* | (2006.01) |
| *F21V 9/08* | (2018.01) |
| *G01N 21/88* | (2006.01) |
| *F21V 5/00* | (2018.01) |
| *F21V 29/70* | (2015.01) |
| *F21V 21/40* | (2006.01) |
| *G01N 21/95* | (2006.01) |
| *F21Y 103/10* | (2016.01) |
| *F21Y 115/10* | (2016.01) |

(52) U.S. Cl.
CPC .............. *F21L 14/02* (2013.01); *F21V 5/007* (2013.01); *F21V 9/083* (2013.01); *F21V 21/406* (2013.01); *F21V 29/70* (2015.01); *G01N 21/8803* (2013.01); *G01N 21/8806* (2013.01); *F21Y 2103/10* (2016.08); *F21Y 2115/10* (2016.08); *G01N 21/9515* (2013.01)

(58) Field of Classification Search
CPC ...... F21V 21/145; F21V 21/406; F21V 9/083; F21L 14/02; F21L 14/023; F21L 14/026; F21L 4/027; F21Y 2103/10; G01N 2021/8816; G01N 21/8803; G01N 21/8806
See application file for complete search history.

(56) References Cited

U.S. PATENT DOCUMENTS

| | | | |
|---|---|---|---|
| 4,770,384 A | 9/1988 | Kuwazima et al. | |
| 7,600,907 B2 * | 10/2009 | Liu | F21V 19/001 362/249.03 |
| 7,950,821 B1 * | 5/2011 | Georgitsis | B60Q 1/0483 362/217.12 |
| 2004/0252501 A1 * | 12/2004 | Moriyama | F21V 19/0025 362/238 |
| 2005/0007778 A1 * | 1/2005 | Lin | F21V 21/32 362/249.07 |
| 2006/0034091 A1 * | 2/2006 | Kovacik | F21L 14/023 362/398 |

(Continued)

*Primary Examiner* — Alexander K Garlen
(74) *Attorney, Agent, or Firm* — Plager Schack LLP; Mark H. Plager; Alexis J. Saenz

(57) ABSTRACT

A lighting system for surface inspection includes an elongated substrate onto which a linear array of lights is mounted to provide extended light coverage. The lights may be dimmable and controlled by a circuit board to reduce veiling glare. A heat sink may disperse heat built up from the linear array of lights. A handle and articulated drop-in pin may provide means to focus all the lights in the same direction and point the lights onto a surface using a single hand or during hands-free use.

5 Claims, 4 Drawing Sheets

(56) References Cited

U.S. PATENT DOCUMENTS

| | | | |
|---|---|---|---|
| 2006/0061991 A1* | 3/2006 | Yeh | B62J 6/02 |
| | | | 362/249.07 |
| 2007/0159819 A1 | 7/2007 | Bayat et al. | |
| 2008/0212319 A1* | 9/2008 | Klipstein | F21L 4/08 |
| | | | 362/231 |
| 2008/0239712 A1 | 10/2008 | Deighton et al. | |
| 2010/0019690 A1* | 1/2010 | Libohova | F21L 14/023 |
| | | | 315/294 |
| 2012/0275154 A1 | 11/2012 | Hood et al. | |
| 2013/0038644 A1 | 2/2013 | Chan et al. | |
| 2014/0036511 A1* | 2/2014 | Whitfield | F21V 27/005 |
| | | | 362/311.02 |
| 2014/0218899 A1* | 8/2014 | Kam Law | F21L 4/027 |
| | | | 362/183 |
| 2017/0002990 A1* | 1/2017 | O'Brien | F21S 8/061 |

\* cited by examiner

LIGHTING SYSTEM WITH GLARE REDUCING LIGHT ARRAY

CROSS REFERENCE TO RELATED APPLICATIONS

This application claims benefit under 35 U.S.C. § 119(e) of U.S. Provisional Application having Ser. No. 62/448,322 filed Jan. 19, 2017, which is hereby incorporated by reference herein in its entirety.

BACKGROUND

The embodiments herein relate generally to lighting, and more particularly to a lighting system with a glare reducing light array.

A test method known as Magnetic Particle Inspection (MPI), requires the application of UV light radiation to illuminate surface defects in metal parts or products. There are three primary problems with current UV inspection lights on the market.

Veiling glare: concentrated hot spots of light reflect excess light back to an inspector's eyes. These bright spots blind inspectors from seeing potential defects and cause eye fatigue from prolonged exposure to high-intensity UV light.

Most inspection lights are packaged in a flashlight style form factor. As such, light sources within the flashlight are arranged in a circular array that results in a beam spot projection thus limiting the viewing area for inspection. However, most parts inspected are not of uniform length and width, meaning the beam spot projection geometry does not adequately cover the area inspected on most parts.

A flashlight requires the user to hold the light with one hand, thus leading to only one hand to handle parts for inspection. If the inspector needs the use of both hands, they either place the flashlight on an open surface or place it on a standard swing arm with a fixed angle, where it does not project optimal illumination to effectively inspect parts.

As can be seen, there is a need for a light apparatus for surface inspection that reduces veiling glare and can be more easily manipulated to cover larger areas during the inspection.

SUMMARY

In one aspect of the subject technology, a lighting system for surface inspection, comprises an elongated substrate; a plurality of lights mounted to the elongated substrate in a linear array, wherein a beam spot of each light overlaps a beam spot of at least one adjacent light mounted to the substrate to form an elongated beam spot; a circuit board attached to the plurality of lights, the circuit board including a control for controlling the amount of light output from the plurality of lights; and a handle attached to the elongated substrate and/or the heatsink for simultaneous movement of the plurality of lights.

In another aspect, a lighting system comprises a housing; an elongated heatsink substrate integrated as a rear wall of the housing; and a plurality of lights mounted to the heatsink, in a linear array, wherein a beam spot of each light overlaps a beam spot of at least one adjacent light mounted to the substrate to form an elongated beam spot, and wherein heat generated by the plurality of lights is absorbed by the heatsink and dispersed toward a rear of the housing.

BRIEF DESCRIPTION OF THE FIGURES

The detailed description of some embodiments of the invention is made below regarding the accompanying figures.

DETAILED DESCRIPTION OF CERTAIN EMBODIMENTS

Figure 1:
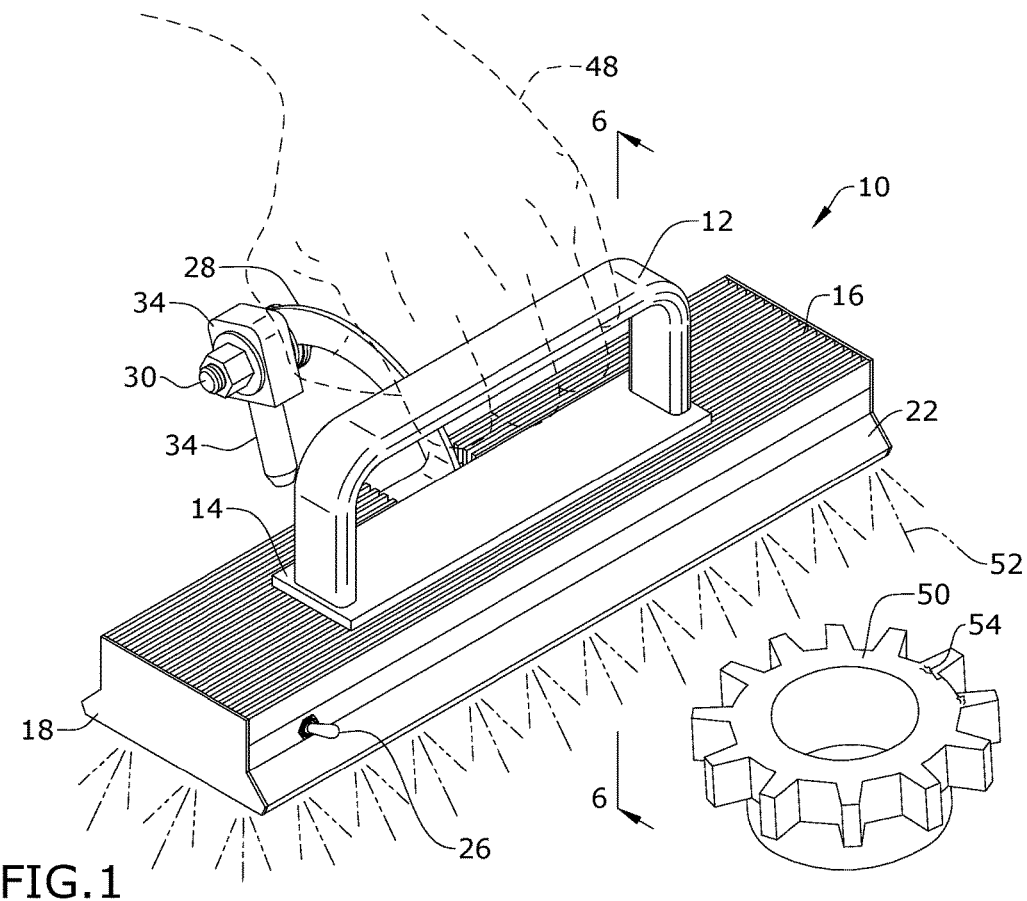
FIG. 1 is a top, front perspective view of a lighting system in accordance with an exemplary embodiment of the subject technology.
Figure 2:
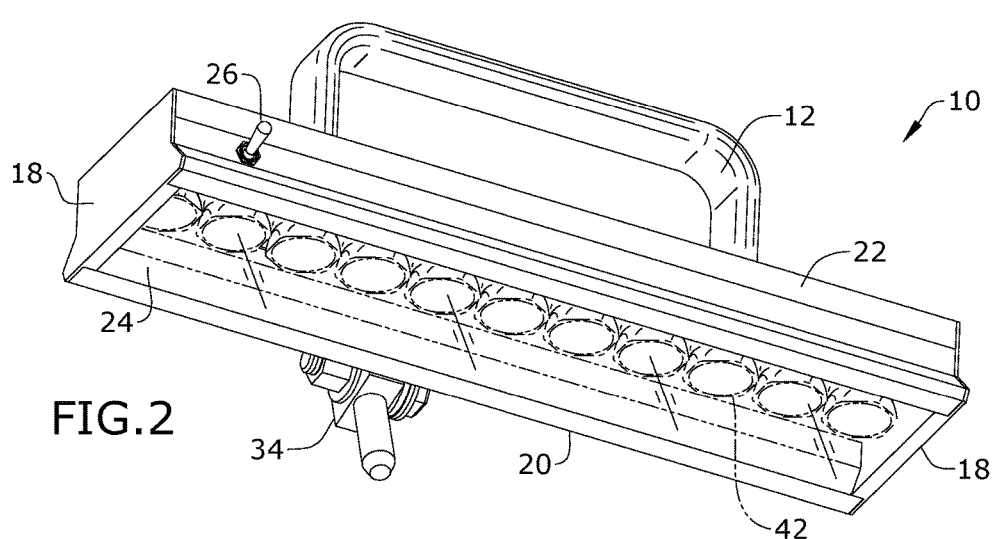
FIG. 2 is a bottom perspective view of the lighting system of FIG. 1.
Figure 3:
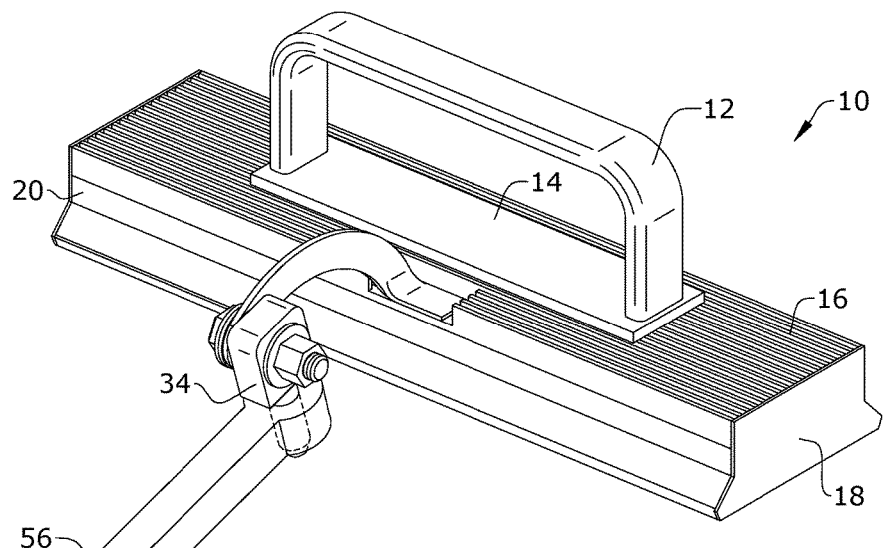
FIG. 3 is a top, rear view of the lighting system of FIG. 1.
Figure 4:
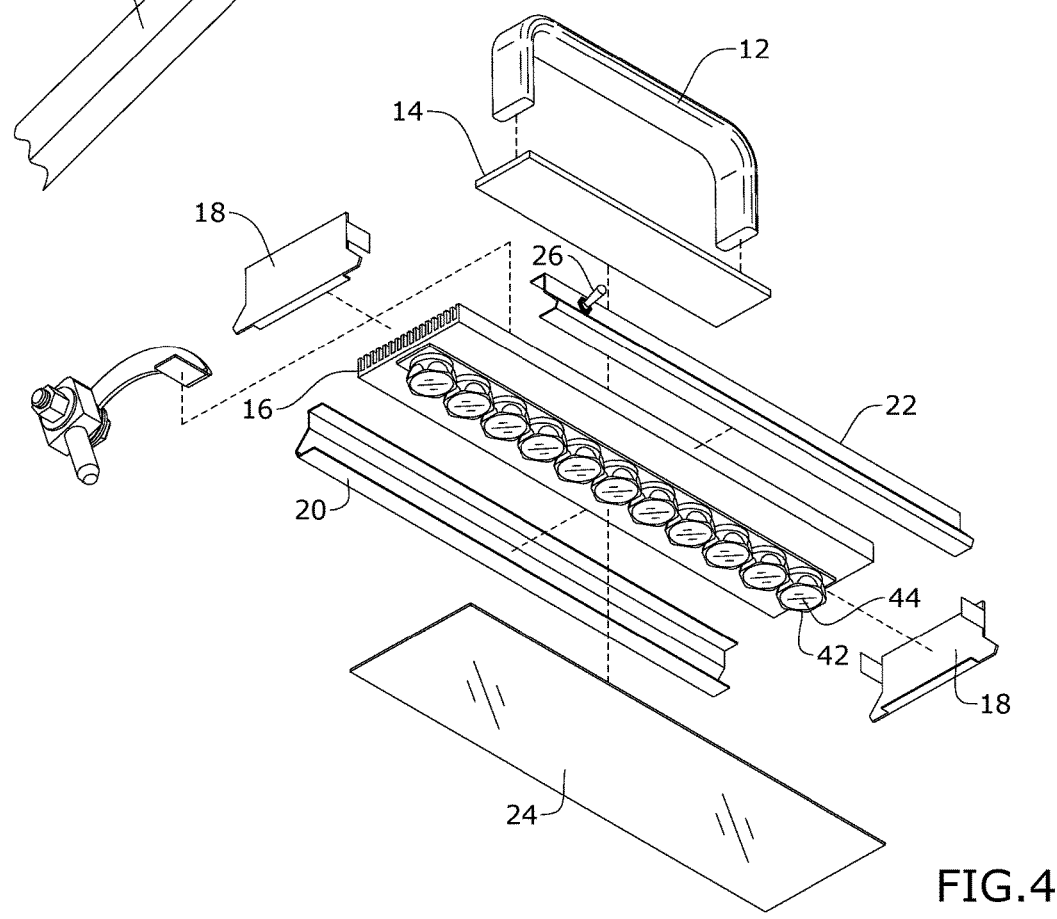
FIG. 4 is an exploded view of the lighting system of FIG. 2.
Figure 5:
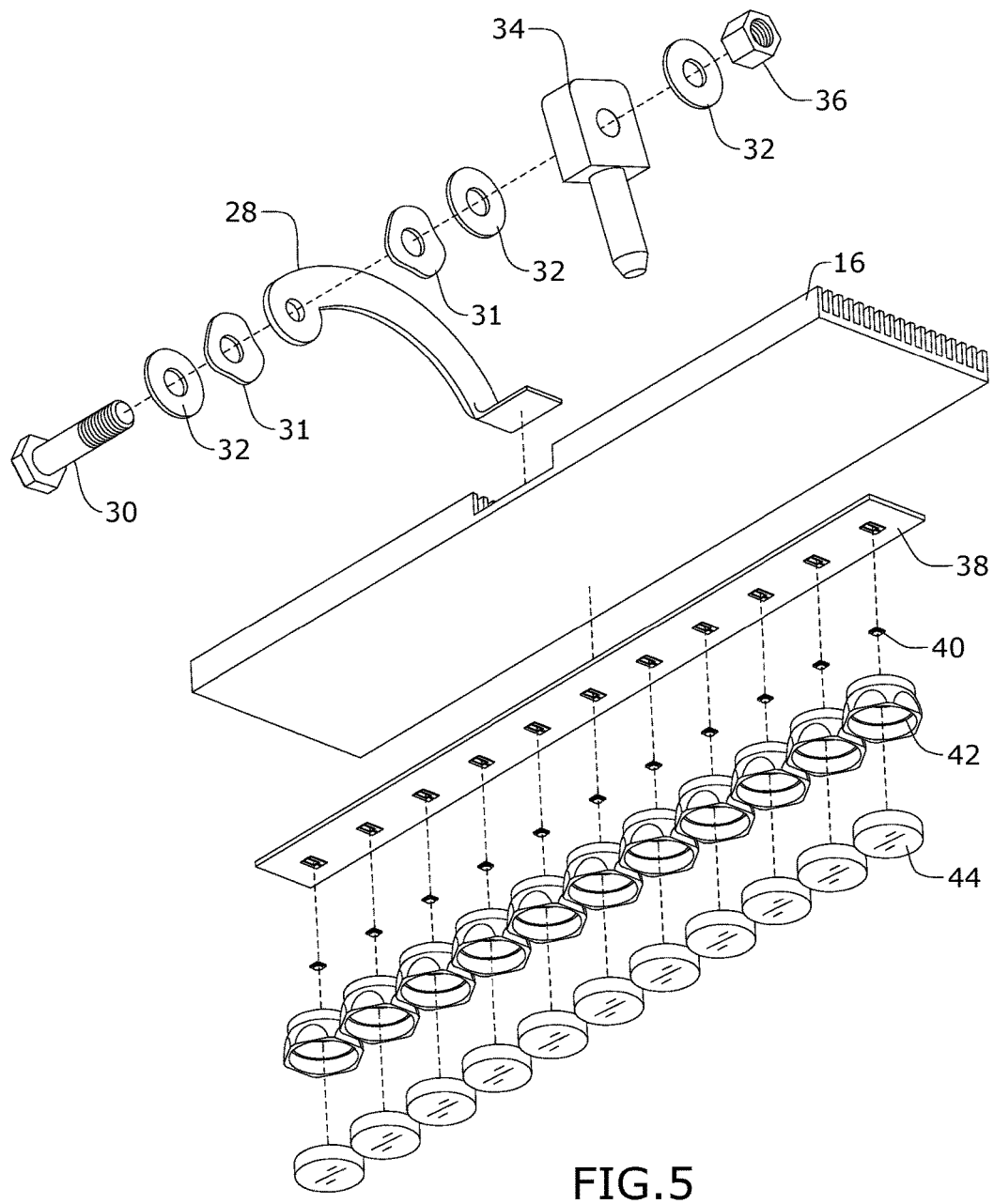
FIG. 5 is an exploded view of a sub-assembly of the lighting system of FIG. 4.

In general, and referring FIGS. 1-7, embodiments of the disclosed subject technology are shown, which provide a lighting system 10 including light sources 40 that are spaced linearly, with consideration for the projection angle of beams, and how each beam crosses another in a manner. As will be appreciated by those of ordinary skill in the art of inspection lighting, this reduces the veiling glare that typically occurs with current inspection lights, thereby eliminating blind spots for the inspector. The linear pattern output produces a light output 52 (for example, an elongated beam spot pattern) that provides coverage of shape and size that more appropriately matches the inspection piece. For example, as shown in FIG. 1, a part 50 is being inspected by shining the light 52 onto a defect 54 (for example, a minute crack in the part 50) that becomes more readily visible by aspects of the lighting system 10. An articulating bracket 28 provides significant angle adjustments of the system 10, which enables the inspector to direct the light where it is most useful. In the example shown, the defect 54 is near an edge between two teeth of the part 50 (a gear). Adjustability of the light angle and the diffusion of overlapping beam spots allows the inspector to see the defect 54 near the part's edge more easily.

In general, the lighting system 10 generally includes a plurality of lights 40 (which can be, UV, white, or IR light depending on the application.) arranged in a linear array mounted onto a common substrate 38. In an exemplary embodiment, the substrate 38 may be a printed circuit board (PCB) connecting the lights to a power source and control circuit. The PCB may be configured to control light intensity so that lights may be dimmable lights by user control which may diffuse light over the inspected area, thus reducing the veiling glare common to prior art lights.

Figure 7:
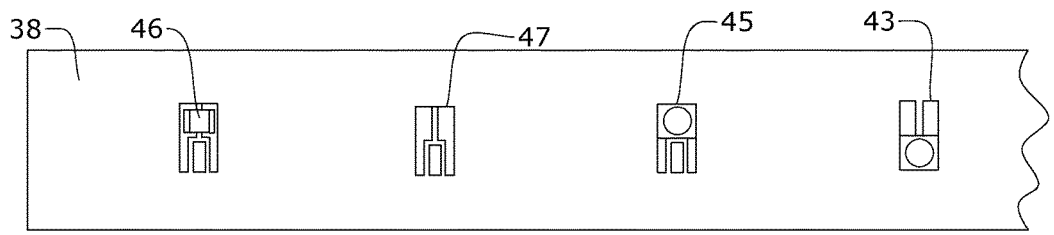
FIG. 7 is a partial, broken view of a jumper strip for connection of lights to a substrate at even intervals in accordance with embodiments of the subject technology.

In some embodiments, the PCB may include evenly spaced solder mounts 47 for receiving the light sources 40, which may be electrically connected via traces (not shown) in the PCB layers (see for example, FIG. 7). The solder mounts 47 may include variable connection options so that different types of light sources may be used in the same system. For example, as will be appreciated, the lighting system 10 is adaptable for various applications that may benefit from different light output simultaneously (or not) from the same light system. For example, the lighting system 10 may include mounts configured for UV lights and visible lights on the same substrate 38. The configurations may include for example, an LED anode, cathode, and neutral heat pad. Another configuration may include an LED connection for an anode and cathode only. As will be understood by those in the art of lighting, one may thus include different light output from the same package which creates flexibility in the applications for which the lighting system 10 may be used. For example, if the lighting system 10 is used in one application for inspection, some of the same lights may be controlled for use in grow applications (for flora) without needing to modify the lighting system 10 or switch to a different lamp.

In addition, in some embodiments, the solder mounts 47 may include zero-ohm jumper resistors 46 which may provide a bridge in a circuit where no LED is present at that soldering position. A user may remove light sources as needed for an application so that there are less lights, but the resistor jumpers 46 maintain the circuit intact. The linear arrangement on the substrate 38 promotes distributed and even coverage of an extended area by the light sources 40 of an inspected surface by overlapping beam spots emanating from the light sources 40. In an exemplary embodiment, the lights sources may be light emitting diodes (LED). In some embodiments, the LEDs may be surrounded by reflective surfaces or housing 42. A bandpass filter lens 44 may cap the LED housing. As will be appreciated, the bandpass filter lenses 44 may help prevent unwanted wavelengths from shining out some of the light sources in embodiments with more than one light type being used.

Figure 6:
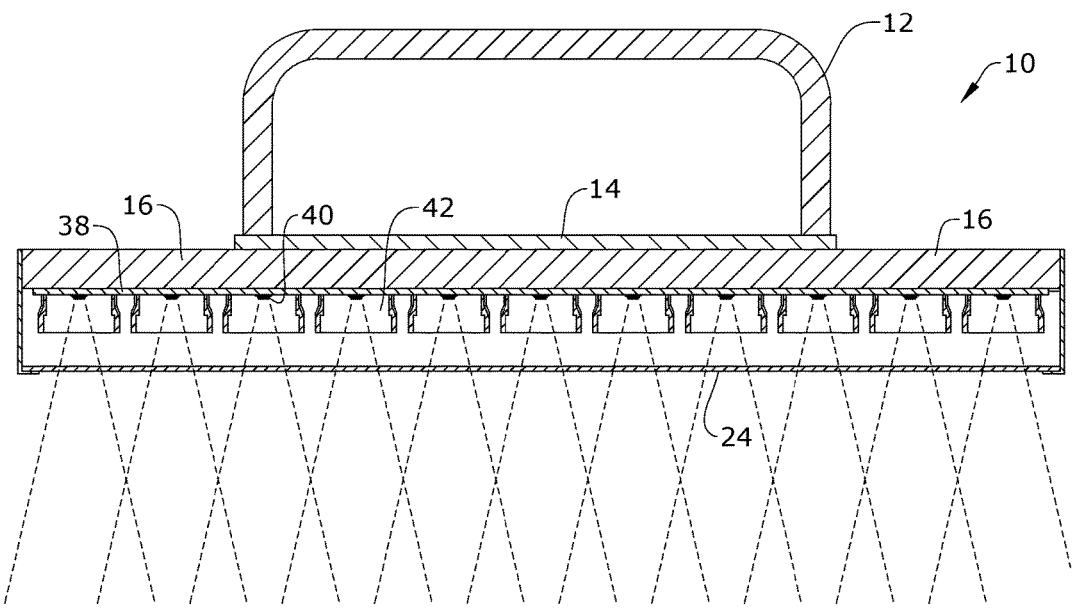
FIG. 6 is a cross-sectional side view of the lighting system taken along the line 6-6 of FIG. 1.

In operation, the reflective surfaces 42 and/or the bandpass filter lens 44 may create a cone-shaped beam of light that projects out at a predetermined viewing angle from respective light sources 40 resulting in a single circular area of light from each light on an inspection surface. In the aggregate, (as shown in FIG. 6), the beam spot from adjacent light sources 40 overlap a short distance from the light system 10 creating (as will be understood) an ellipse shaped beam spot. The bandpass filter lens 44 may be selected depending on the application so that either IR, UV, and/or visible light is provided.

The substrate 38 may be attached to an aluminum heatsink 16 which may be larger than the substrate 38 to diffuse heat from the lights 40 over an extended area. In some embodiments, the heatsink 16 may be a rear wall of the housing for the lights 40. In some embodiments, the heatsink wall 16 may be coupled to end panels 18 and front and rear panels 20 and 22 to surround the substrate 38 and lights 40. The heatsink 16 may include a plurality of fins to draw heat from the lights 40 toward the rear of the housing and cool the heated fins by allowing air to pass through the fin channels. A three-way switch 26 on one of the panels walls 18, front panel 20, or rear panel 22 may be electrically connected to the PCB and lights 40. The three-way switch 26 may be connected to the circuit in the PCB (described above) to control (in different configurations) a first set of lights of a first type among the light sources 40 being on, a second type among the light sources being on and a combination of all light types being on. In an alternate embodiment, the three-way switch may control on, off, and dimmed settings. A clear face guard 24 may be secured by the panels 18, 20 and 22 to cover and protect the internal components including the lights 40 from contact by the environment.

A bracket handle 12 with a handle plate 14 may be mounted to the outward facing surface of heatsink 12 (on a side of the heatsink 12 opposite the lights). The handle 12, as may be appreciated, allows the user to point a plurality of lights with a single hand during an inspection, thus freeing up the other hand for other responsibilities.

In an exemplary embodiment, a center bracket 28 may be attached to the housing (for example, to the heatsink 12 wall). An articulating drop-in pin 34 may be mounted to the bracket 28 to provide articulated movement. In some embodiments, the drop-in pin 34 is configured to drop into the receiving end of a swing arm 56 (see FIG. 3). When attached to the swing arm 56, it will be appreciated that the system 10 is ready for adjustable, hands-free use during inspection of a surface. The combination of the center bracket 28 and drop pin 34, form a flexible joint held together by fasteners (for example a bolt 36, nut 30 and washers 32 and a wave spring 31 that adds tension to the joint. The drop-in pin 34 assembly allows the light to be set at a desired angle by the operator so that the light is positioned for optimal and close-up inspection of a surface section.

Figure 8:
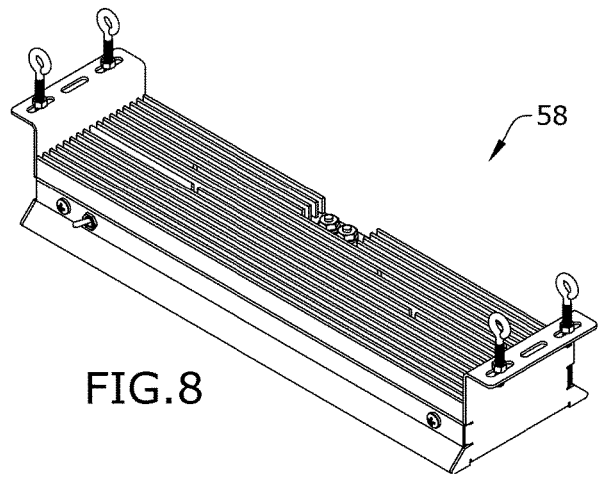
FIG. 8 is a top, front perspective view of a lighting system in accordance with an alternate exemplary embodiment of the subject technology.

Referring now to FIG. 8, a lighting system 58 is shown according to another embodiment. The lighting system 58 is similar to the lighting system 10 except that it is configured to mount from flat surfaces such as walls or ceilings. Some embodiments include eyelets on the housing. The lighting system 58 may be hung from a structure by inserting a chain or rope through the eyelets to provide hands-free use of system.

Persons of ordinary skill in the art may appreciate the numerous design configurations that may be possible while enjoying the functional benefits of the inventive systems. Thus, given the wide variety of configurations and arrangements of embodiments of the present invention, the scope of the invention is reflected by the breadth of the claims below, rather than narrowed by the embodiments described above. While some details of the accompanying figures are not described above, their use and configuration are understood by those of ordinary skill in the art and are part of the disclosure herein.

What is claimed is:

1. A lighting system for surface inspection, comprising:
an elongated substrate;
a plurality of lights mounted to the elongated substrate in a linear array, wherein a beam spot of each light overlaps a beam spot of at least one adjacent light mounted to the substrate to form an elongated beam spot;
a circuit board attached to the plurality of lights, the circuit board including a control for controlling the amount of light output from the plurality of lights;
a handle attached to the elongated substrate for hand-held use during inspection of a surface;
an articulated bracket, wherein a first end of the articulated bracket is coupled to the elongated substrate;
a drop-in pin, wherein a second end of the articulated bracket is coupled to the drop-in pin; and
a swing arm, wherein the drop-in pin is freely removable from an opening in the swing arm and, wherein the articulated bracket is configured to, when coupled to the swing arm, to provide an adjustable angle and provide simultaneous articulated movement of the plurality of lights for hands-free use during inspection of the surface.

2. The lighting system of claim 1, further comprising a heatsink mounted to the elongated substrate for dispersing heat generated by the plurality of lights.

3. The lighting system of claim 1, wherein the circuit board includes a control to dim the plurality of lights.

4. The lighting system of claim 1, wherein the plurality of lights is attached to the elongated substrate at an even spacing between each light.

5. The lighting system of claim 1, further comprising:
   a first solder pad mount on the circuit board configured to receive a first type of light source in the linear array; and
   a second solder pad mount on the circuit board configured to receive a second type of light source in the linear array, wherein the second type of light source is different than the first type of light source.

\* \* \* \* \*